United States Patent
Gokhale et al.

(10) Patent No.: US 10,925,929 B2
(45) Date of Patent: Feb. 23, 2021

(54) METHOD TO MODULATE PIGMENTATION PROCESS IN THE MELANOCYTES OF SKIN

(75) Inventors: Rajesh Sudhir Gokhale, Delhi (IN); Vivek Tirunelveli Natarajan, Delhi (IN); Parul Ganju, New Delhi (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 1198 days.

(21) Appl. No.: 14/117,519

(22) PCT Filed: May 16, 2012

(86) PCT No.: PCT/IB2012/052456
§ 371 (c)(1),
(2), (4) Date: Aug. 11, 2014

(87) PCT Pub. No.: WO2012/156927
PCT Pub. Date: Nov. 22, 2012

(65) Prior Publication Data
US 2014/0348788 A1    Nov. 27, 2014

(30) Foreign Application Priority Data
May 16, 2011    (IN) .......................... 1420/DEL/2011

(51) Int. Cl.
*A61K 38/21*    (2006.01)
(52) U.S. Cl.
CPC ................................ *A61K 38/217* (2013.01)
(58) Field of Classification Search
None
See application file for complete search history.

(56) References Cited

U.S. PATENT DOCUMENTS 8,221,766 B2 *  7/2012  Dryer .................. A61K 8/97
424/195.18

OTHER PUBLICATIONS

Kolchanov, 1988, Journal of Molecular Evolution, vol. 27, pp. 154-162.*
Pasquo, 2012, PLoS One, vol. 7, Issue 2, e32555.*
Bork, 2000, Genome Research 10:398-400.*
Bork et al., 1996, Trends in Genetics 12:425-427.*
Interferon gamma Roche Cat No. 11040596001(2010).*
Kovarik et al. (2005). Melanoma Research vol. 14, No. 6, pp. 481-488.*
Maluish et al. (1988), Journal of Clinical Oncology, vol. 6, No. 3, pp. 434-445.*
Schneider et al. (1995), Arch Gynecol. Obstet., vol. 256, pp. 75-83.*
Koeffler et al., (1984), PNAS, vol. 81, pp. 4080-4084.*
Osamura et al. (1980), Am. J. Clin. Pathol., vol. 74, pp. 239-242.*
V.T. Natarajan et al., PNAS., vol. 111(6), p. 2301-2306. (Year: 2004).*
Platanias et al. Nat Rev Immunolo. 5(5), p. 375-86. (Year: 2005).*
Ulasov et al. 2018, J. of Controlled Release, vol. 269, pp. 24-35. (Year: 2018).*
Son et al., 2013, Pigment Cell Melanoma Res. 27:201-208 (Year: 2013).*
Zhou et al.,2016, Biol. Pharm. Bull., 39, 1091-1099 (Year: 2016).*

* cited by examiner

*Primary Examiner* — Gary B Nickol
*Assistant Examiner* — Jegatheesan Seharaseyon (57) ABSTRACT

The invention describes a method to modulate melanosome maturation process in melanocytes. Further, it describes a method to reversibly alter the process of pigmentation in the human epidermal skin. The method targets melanosome maturation and its transfer to keratinocytes, which are key processes involved in the pigmentation for its potential use in predictable and controlled regulation of pigmentation in human skin.

10 Claims, 2 Drawing Sheets

Specification includes a Sequence Listing.

METHOD TO MODULATE PIGMENTATION PROCESS IN THE MELANOCYTES OF SKIN

FIELD OF THE INVENTION

The invention involves modulating visible pigmentation of skin. The present invention deals with the role of IFN-γ in stalling the maturation of melanosomes at stage I and II leading to hypopigmentation and restoring the process on its removal. The overall pigmentation process consists of melanosome formation in early stages I and II, melanin synthesis, melanosome maturation and subsequent transfer of melanosomes to keratinocytes. The process of melanosome maturation can be modulated in a predictable manner by controlling the concentrations of IFN-γ. The current invention relates to the use of IFN-γ and its agonists and antagonists in modulating pigmentation in humans for clinical or cosmaceutical purposes.

BACKGROUND OF THE INVENTION

Pigmentation is a unique process involving two cell types from human epidermis—melanocytes and keratinocytes. Melanocytes produce melanin polymers inside an organelle, melanosome, through a series of distinctly defined programmed concerted steps and then transfer pigmented melanosomes to keratinocytes (Hu et al., 2007). The pigment observed in the skin is due to the presence of melanosomes in keratinocytes. The complete process of pigmentation can be broadly divided into four distinct biological processes— 1) initiation of melanosome formation 2) melanosome maturation in stages I, II, III and IV involving trafficking of several proteins 3) melanin biosynthesis in stage III and IV of melanosomes maturation 4) transfer of stage III and IV melanosomes to keratinocytes. Disruption in any of these steps can lead to altered levels of skin pigmentation. Maturation of organelles is a very important component of cellular programming in human body. In the present invention, we show that interferon-γ (IFN-γ) directly regulates the process of melanosome maturation and transfer from melanocytes, thereby affecting the complete process of skin pigmentation. Hypopigmentation as well as hyperpigmentation are clinical manifestations of various pathological conditions and are also of cosmetic importance. Induction of pigmentation is considered a regulated differentiation program of melanocytes. Studies in the past have identified several genes involved in this process. Many of these observations have originated from mouse genetics and currently close to 120 loci are known to be involved in the regulating pigmentation (Bennett and Lamoreux, 2003). Of these, Tyrosinase (TYR), Tyrosinase related protein-1 (TYRP1/TRP-1) and Dopachrome tautomerase (DCT/TYRP2) are the enzymes that catalyze melanin synthesis. The key transcription factor MITF is known to orchestrate the events during melanogenesis through these three central enzymes. Some of the cues for triggering the cells to initiate and sustain melanin synthesis are also well known. Melanotropic factors like HGF, SCF, ET are secreted by neighbouring keratinocytes and fibroblasts (Yamaguchi et al., 2007; Yamaguchi and Hearing, 2009). These factors regulate cell proliferation and melanogenesis. α-MSH signalling appears to be central based on multiple lines of evidence from genetic to animal model studies. Recently it has come to light that α-MSH secretion by keratinocytes is mediated by p53 and thereby the control of pigmentation occurs in a paracrine manner (Cui et al., 2007). The interconnections between signalling pathways that positively regulate melanogenesis are complex and are only beginning to be understood. The well studied hyperpigmenting condition is exposure of skin to UV rays, that triggers a series of short and long term effects that result in increased pigmentation (Choi et al., 2010). This response includes secretion of melanogenic factors and increase in melanocyte dendricity in anticipation of melanosomal transfer (Scott et al., 2006). It is surprising that so many pathways and effectors are known to increase pigmentation, but very little is known about active reversal of this process.

Multiple lines of evidence suggest presence of melanocytes with decreased pigment under physiological and patho-physiological conditions. Developmentally, melanocytes initiate from the neural crest as non-pigmented precursor cells. These cells migrate to skin and become pigmented melanocytes. A rare manifestation of malignant melanoma in the form of amelanotic lesions is observed and is often associated with poor prognosis. Similarly cells bearing lesser amount of the melanin are detected when melanocytes are cultured under defined conditions in vitro and these cells have been termed as melanoblasts. Further, clinical conditions like post-inflammatory hypopigmentation are known where melanin is temporarily lost from the skin. The pathways by which pigmentation is actively suppressed in these conditions remains to be investigated. It is also not clear whether melanin synthesis is the only step where pigmentation is regulated, several studies indicate that the regulation of pigmentation could be brought about at the level of 1) melanosome maturation 2) melanosome dispersal within cells (Richardson et al., 2008) 3) transfer of melanosomes from melanocytes to keratinocytes (Seiberg et al., 2000) 4) degradation/removal of melanin from the cells.

Decreasing melanin content is of importance from a cosmaceutical perspective. Despite this, agents that could suppress or reverse the pigmented state are limited. It is not clear whether shutting down melanogenesis through MITF alone is sufficient to reverse the default pigmented state. Alternately, there could be pathways actively suppressing the melanogenesis program independent of MITF. Using appropriate model systems and with the wealth of information available from the biology of pigment cells, it is currently possible to recreate cellular changes and understand these using holistic approaches. There are a number of compounds known that interfere with the process of pigmentation. Among them the main class of molecules belong to the category of melanogenesis inhibitors. These compounds reversibly inhibit TYR enzyme and result in decreased melanin content. Molecules like kojic acid belong to this category. The other class of compounds could be classified as suicide substrates; inhibitors that in fact are substrates for TYR but do not participate in further melanin synthesis or are irreversible inhibitors. Molecules like hydroquinones and their derivatives that represent this category of inhibitors are extensively used, but they have undesirable side effects as they interfere with other cellular processes as well. Another class of compounds act by targeting the TYR protein level. These compounds cause the protein to misfold, thereby reducing its activity. Many other small molecule inhibitors are known to decrease melanogenesis and some of their functions are well characterized. One of the main side effects of inhibiting melanogenesis is the leaking of intermediates resulting in cell cytotoxicity, which could trigger autoimmunity. Therefore a more biological way of controlling melanogenesis is very much sought by the cosmetic industry.

There are very few pathways known by which cells that make melanin can be made to reduce the level of pigmentation. In this invention we have disclosed how cells maintain a hypopigmented state by use of the interferon pathway. Microarray suggested that many of the genes involved in pigmentation, like TYRP1, TYRP2/DCT, cappuccino (CNO), HPS4, G-protein coupled receptor 143 (GPR143), OCA2, SLC7A11 and mucolipin 3 (MCOLN3) are down-regulated by IFN-γ and downstream effectors of IFN-γ such as IFNGR1, IFNGR2, STAT-1, JAK 1, JAK2, IRF-1, IRF-3, IRF-7, IRF-9, PSMB8 and PSMB9 are induced. Cell biological investigation suggested that hypopigmented cells have fewer mature melanosomes. The analysis of the melanosomal proteins indicated a decrease in TYR and DCT/TYRP2 levels. IFN-γ also alters the transfer of mature melanosomes from melanocytes to keratinocytes. Therefore targeting IFN-γ mediators either pharmacologically using small molecule inhibitors or the cytokine itself would result in controlled pigmentation response. The main advantage of this method would be the use of existing biological pathway that mediates hypopigmentation without altering MITF levels. IFN-γ functions like a rheostat in calibrating skin pigmentation. Hence the system would be adjusted to suit the change. We have demonstrated that this pathway, by stalling the process of melanosome maturation affects all the downstream functions, resulting in hypopigmentation. Therefore targeting this pathway would result in concerted reduction in melanosomes and be a more natural way of achieving hypopigmentation.

Of the other pathways known to cause hypopigmentation include the TGF-β pathway (Martinez-Esparza et al., 2001). It was demonstrated that the cultured B16 cells are effectively hypopigmented by using TGF-β. This was associated with a decrease in the content of mature melanosomes in the cell. This study was followed up with mouse experiments recently (Nishimura et al., 2010). However the studies confirmed that this reduction was due to decrease in the levels of the key transcription factor MITF and results in the maintenance of stem cells. A mechanism of site-specific hypopigmentaion is observed in the palmoplantar skin, where dermis derived DKK1 suppresses WNT signalling, altering MITF levels and melanocyte growth (Yamaguchi et al., 2009). On the other hand, our studies demonstrate that IFN-γ alters pigmentation without altering MITF levels, indicating that the mechanism by which IFN-γ mediates hypopigmentation is distinct from TGF-β and DKK1. Therefore use of interferon pathway would be a much more predictable and efficient way to achieve altered pigmentation.

Earlier reports that support our claim include the generation of a mouse transgenic line wherein the mice overexpress IFN-γ in the epidermis. These mice apart from having other discernible phenotype are conspicuously hypopigmented in the hair (Carroll et al., 1997). The authors had not investigated the mechanism in this study and as mice do not have epidermal pigmentation, the function of this pathway in skin epidermal melanocytes was not known previously. Most of the earlier studies on the effect of IFN-γ have been performed on transformed melanoma cells which have been proven to have different properties than normal human epidermal melanocytes (Nihal et al., 2005). The role of IFN-γ in altering melanoma-associated antigen presentation has been proposed to alter inflammatory responses and hamper effective recognition of melanoma cells (Le Poole et al., 2002). An earlier study on human malignant melanoma cells had indicated statistically non-significant role of IFN-γ in the melanin synthesis decrease in these transformed cells (Garbe et al., 1990). While melanin synthesis is one of the processes involved in pigmentation, visible skin color is a complex phenomenon involving cascade of distinct biological events. Our studies show an important role of IFN-γ in regulating pigmentation by stalling the maturation of the key melanocyte organelle, melanosomes in cultured human melanocytes. In an altogether different system, IFN-γ is a potent inducer of catagen-like changes in cultured human anagen hair follicles (Ito et al., 2005). Recently using zebrafish as a model system toll like, receptor pathway was identified to result in hypopigmentation of melanocytes (Jin and Kang, 2010). Though the observations are limited it does highlight how signalling pathways regulates pigmentation. Interferons themselves are known to exert their effect by the induction of a family of transcription factors, Interferon Regulatory Factors (IRFs). In a recent study, IRF-4 was found to be associated with pigmentation in the European population (Sturm, 2009). These observations further strengthen our claim on the involvement of interferon pathway members functioning to reduce skin pigmentation. Therefore we propose to patent the process of achieving altered pigmentation of skin and derived melanocytes by targeting members belonging to IFNG, IFNGR1, IFNGR2, STAT-1, JAK 1, JAK2, IRF-1, IRF-3, IRF-7, IRF-9, PSMB8 and PSMB9. In the current invention, we have developed a process to achieve controlled pigmentation through IFN-γ peptide and its downstream proteins or by using various agonist or antagonist of IFN-γ pathway.

OBJECTS OF THE INVENTION

The main object of the invention is to develop a reversible method to modulate visible pigmentation of skin.

Another object of the invention is to develop a reversible method to modulate melanosome maturation in melanocytes.

Another object of the invention to develop a method to modulate melanosome transfer to keratinocytes.

Another object of the invention to develop a method to modulate melanosome maturation in the epidermal skin melanocytes by identifying downstream targets of the agent that affects melanosome maturation.

SUMMARY OF THE INVENTION

Accordingly, the present invention relates to a reversible method to modulate visible pigmentation of skin. The present invention results from studies demonstrating that the peptide IFN-γ can inhibit melanosome maturation and transfer from melanocytes and thus reduces the level of pigmentation. Increased levels of IFN-γ supplied as recombinant peptide decreases the levels of TYR, TYRP1 and TYRP2/DCT along with several other melanosomal proteins, CNO, HPS4, GPR143, OCA2, SLC7A11 and MCOLN3, thereby altering the process of melanosome maturation. Application of IFN-γ to normal melanocytes in vitro results in marked decrease in the maturation of melanosomes and resultant hypopigmentation in these cells. The present invention thus relates to a method of altering the process of melanosome maturation leading to alteration in pigmentation. The present method is useful in clinical situations of hyperpigmentation due, for example, to sun-exposure, inflammation, or scarring or due to disorders with congenital or acquired proliferations of melanocytes. IFN-γ is produced in the epidermis under certain conditions, thus it can be applied locally to the epidermis as well as systemically administered. Problems with increased or aberrant skin pigmentation are common and widespread. Such changes may still cause significant distress even when localized to small area of the skin, especially when aberrant pigmentation involves the face and/or hands. Here we reveal a process of hypopigmentation brought about by the use of a peptide IFN-γ and its downstream target proteins such as IFNGR1, IFNGR2, STAT-1, JAK 1, JAK2, IRF-1, IRF-3, IRF-7, IRF-9, PSMB8 and PSMB9 etc. Further we disclose that this factor is sufficient to replicate the suppression of pigmentation response in these cells. Microscopic evaluation suggests the presence of immature melanosomes when cells are treated with IFN-γ. Therefore IFN-γ induces a hypopigmented state by actively suppressing melanosome maturation through a concerted effect on key targets involved in pigmentation.

BRIEF DESCRIPTION OF THE DRAWINGS AND TABLES

Figure Legend 1

Electron micrographs of primary normal human melanocytes were treated with 100 U/ml IFN-γ using transmission electron microscope. (a) Control (untreated) melanocyte (b) treated with 100U/ml IFN-γ. Melanocytes were fixed, permeabilized and the melanosomes probed using HMB45 antibody for melanosomal matrix (green) and melanin (red) (c) control (d) 100 U/ml IFN-γ treated melanocytes. Quantified image normalized fluorescence intensity of (e) HMB45 and (f) melanin staining of melanocytes.

Figure Legend 2

(a) Primary human melanocytes treated with 100 U/ml IFN-γ followed by microarray analysis of regulated genes represented as heat-map. Some of the conspicuously down-regulated genes include DCT, Mlan A and Trp1. Notably many genes involved in immune functions were upregulated by the treatment. (b) Real time PCR analysis of regulated genes under two different concentrations of IFN-γ (100 U/ml and 200 U/ml). (c) Western blot analysis of DCT, phosphorylated STAT-1, phosphorylated GSK-3β from control, MSH (6 nM) or IFN-γ (100 U/ml) treated melanocytes.

DETAILED DESCRIPTION OF THE INVENTION

IFN-γ stalls the maturation of melanosomes by altering the levels of key proteins involved in melanosome formation and maturation, like TYR, TYRP1, and DCT/TYRP2, CNO, HPS4, GPR143, OCA2, SLC7A11 and MCOLN3, thus decreasing pigmentation in normal human melanocytes. Modulation of pigmentation protein levels by IFN-γ can be useful in attaining hypopigmented states.

Another determinant of skin pigmentation is the transfer of mature (Stage III and IV) melanosomes from melanocytes to keratinocytes. Our in-vitro studies using melanocyte-keratinocyte co-culture models, demonstrates that that IFN-γ decreases this transfer process, altering the number of melanosomes in keratinocytes, leading to decreased apparent pigmentation.

As detailed in Example 5 later, this mechanism of IFN-γ mediated hypopigmentation may be apparent in several hypopigmentary conditions of skin, like tuberculoid leprosy, where localised concentrations of IFN-γ can inhibit melanosomes maturation and transfer in the melanocytes of the lesional skin. Targeting this pathway would thus be of therapeutic importance for the treatment of hypopigmentary conditions. Alternately, mimicking this pathway would promote controlled pigmentation of skin by targeting melanosome maturation in melanocytes and the transfer of melanosomes to keratinocytes.

IFN-γ can be formulated as a composition using a variety of physiologically acceptable carriers, excipients or diluents. The composition can be, for example, in a cream, gel or lotion for topical use or can be present as a liquid. The composition can also be present in dosage unit form that could be administered through sub-cutaneous infusion if necessary.

Since TGF-β has previously been shown to inhibit melanin synthesis in B16 melanoma cells as well as human primary melanocytes (Martinez-Esparza et al., 2001; Nishimura et al.; Nishimura et al., 2010) Therefore it was important to determine whether IFN-γ acted via a mechanism involving TGF-β. It was reported that TGF-β causes reduction in pigmentation by reducing the level of MITF transcription factor. However IFN-γ and its downstream effector proteins achieve hypopigmentation despite having unaltered levels of MITF. These findings indicate that IFN-γ mediated hypopigmention process is different from that brought about by TGF-β.

The generalizability of the hypopigmenting functions of IFN-γ is demonstrated by its inhibitory effect on a overall pigmentation process involved in normal human melanocytes. IFN-γ is locally produced in the epidermis in several conditions (Sarra et al., 2011). Others have previously demonstrated that keratinocyte-derived factors, which are also locally produced, influence melanocyte behaviour, like melanocyte proliferation, dendricity, and the amount of melanin produced (Gordon et al., 1989). Thus taken together, the data provided herein indicate that local administration of IFN-γ could be used for predictably alter pigmentation in human epidermal cells.

The present disclosure provides details of how IFN-γ can be used to reversibly modulate melanosome maturation occurring in stage I and II in epidermal melanocytes. This disclosure makes it obvious that derivatives, mimics or antagonists of IFN-γ can also be used to reversibly modulate melanosome maturation occurring in stage I and II in epidermal melanocytes. The present specifications therefore do not limit the scope of the invention to IFN-γ, and instead extends the scope to derivatives, mimics and antagonists of IFN-γ.

Accordingly, the present invention is directed towards a method to reversibly alter melanosome maturation occurring in stage I and II in an epidermal melanocytes in a subject by contacting or withdrawing IFN-γ and its derivative, mimic, antagonist thereof with said melanocytes in a controlled manner, and wherein the IFN-γ and derivative, mimic, antagonist thereof modulate the expression of IFN-γ pathway components selected from a group comprising IFNGR1, JAK1 and STAT1.

In yet another aspect of the invention IFN-γ, or its derivative, or its mimic, or an antagonist, or components of IFN-γ pathway are contacted with melanocytes in the range of 100-500 U/ml for a period in the range of 1 to 10 days.

In yet another aspect of the invention IFN-γ or its derivative, or a mimic or an antagonist of IFN-γ reversibly alters the levels of TYR, and TYRP2/DCT, CNO, HPS4, GPR143, OCA2, SLC7A11 and MCOLN3.

In further aspect of the invention the transfer of melanosome to keratinocytes is altered by targeting components of IFN-γ pathway selected from the group comprising of IFNG, IFNGR1, JAK1 and STAT1.

In an additional aspect of the invention the use of IFN-γ and its components and its agonists and antagonists in modulating pigmentation in humans for clinical or cosmaceutical purposes.

In yet another aspect of the invention a method of treating skin pigmentation by administering to a subject IFN-γ or its derivative, or a mimic or antagonist of IFN-γ.

In further aspect of the invention IFN-γ or its derivative, or a mimic or an antagonist of IFN-γ is administered to the subject by topical delivery or by sub-cutaneous delivery.

In yet another aspect of the invention the topical delivery or sub-cutaneous delivery is in a dosage form selected from the group comprising, a powder, a solution, an emulsion, a fluid emulsion, a suspension, a fluid suspension, a semi-solid, an ointment, a paste, a cream, a gel, a jelly, a foam, an implant, an injection, a patch and a spray.

In an additional aspect the invention is useful for treating skin disorders selected from the group comprising of hyperpigmentation, hypopigmentation, uneven pigmentation, post inflammatory pigmentation, sun-damaged skin, pigmented birthmark, acanthosis nigricans and solar lentiges, age-related pigmentation changes, indeterminate leprosy, tuberculoid leprosy, borderline leprosy, leprematous leprosy.

The following examples are given by way of illustration of the present invention and therefore should not be construed to limit the scope of the present invention.

Example 1

Figure 1:
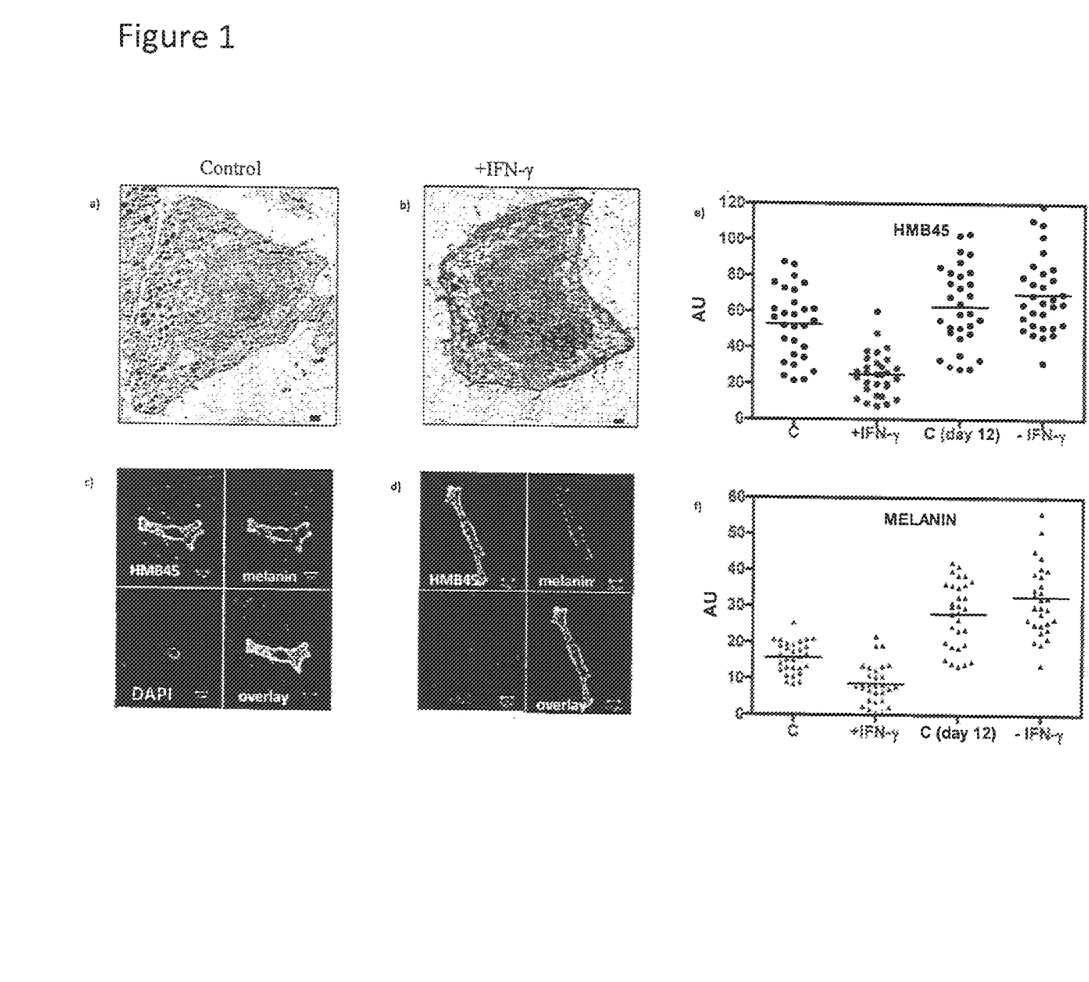

Cultures of normal human epidermal melanocytes (NHEM) (procured from Lonza, or established from epidermis) were maintained in M254 medium containing PMA-free supplements (Invitrogen), at 37° C., in 5% $CO_2$. To study the effect of IFN-γ on melanocytes, early passage cultures of melanocytes were grown in the presence or absence of recombinant human IFN-γ (Peprotech) at a dose of 100 U/ml and the cells were observed after 8 days of treatment. Decreased pigmentation could be observed in the cell pellets treated with IFN-γ, confirming the presence of a mechanism for the induction of hypopigmentation (FIG. 1). To understand the molecular targets of human IFN-γ (henceforth referred to simply as IFN-γ) in melanocytes and the mechanism by which the cells are hypopigmented further studies were carried out.

Melanosome maturation status in the cells and visible pigmentation are tightly linked together. The process of melanin synthesis is sequestered in the late stages of melanosome maturation and requires a proper targeting of multiple proteins to early stages of melanosomes for initiation. The status of melanosomal receptivity for the synthesis of melanin and the content of melanin within each melanosome could therefore be considered as cellular endpoint of pigmentation program. Since melanin is an electron dense substance, visualization of melanosomes is classically carried out using electron microscopy. The technique allows identification of distinct stages of melanosomes I to IV based on the organelle architecture and melanin content. IFN-γ treated cells (as mentioned above) were subjected to electron microscopy and confocal imaging using HMB45 and melanin antibody. Electron microscopic evaluation was carried out on control and IFN-γ treated cells. Analysis of the micrographs suggested that fewer stage III and IV melanosomes were detected in IFN-γ treated cells, whereas several could be distinctly identified in control cells. For finer and quantitative analysis of the status of melanosomes immunocytochemical approach was adopted. Control and IFN-γ treated primary melanocytes were stained with Human melanoma Black 45 (HMB45) from (Dako Cytomation) and anti-melanin antibody (rabbit polyclonal raised against synthetic melanin, raised in the laboratory). Nuclei were counterstained with DAPI (4',6-diamidino-2-phenylindole) (Invitrogen) and the cells observed under confocal microscope. Recurrent observations indicated that lesser fluorescence signals were obtained from IFN-γ treated cells. For comparative quantitation, processing and imaging of control and IFN-γ treated cells was carried out under identical conditions. The settings used for imaging like background correction, signal to noise ratio etc are arbitrary and were kept constant. Mean fluorescence intensity of DAPI was subtracted from HMB45 or melanin signals from each cell for normalization. Comparison of the normalized intensities indicated that IFN-γ treated cells had significantly less melanin content as well as melanosome matrix as detected by HMB45 antibody.

Example 2

Figure 2:
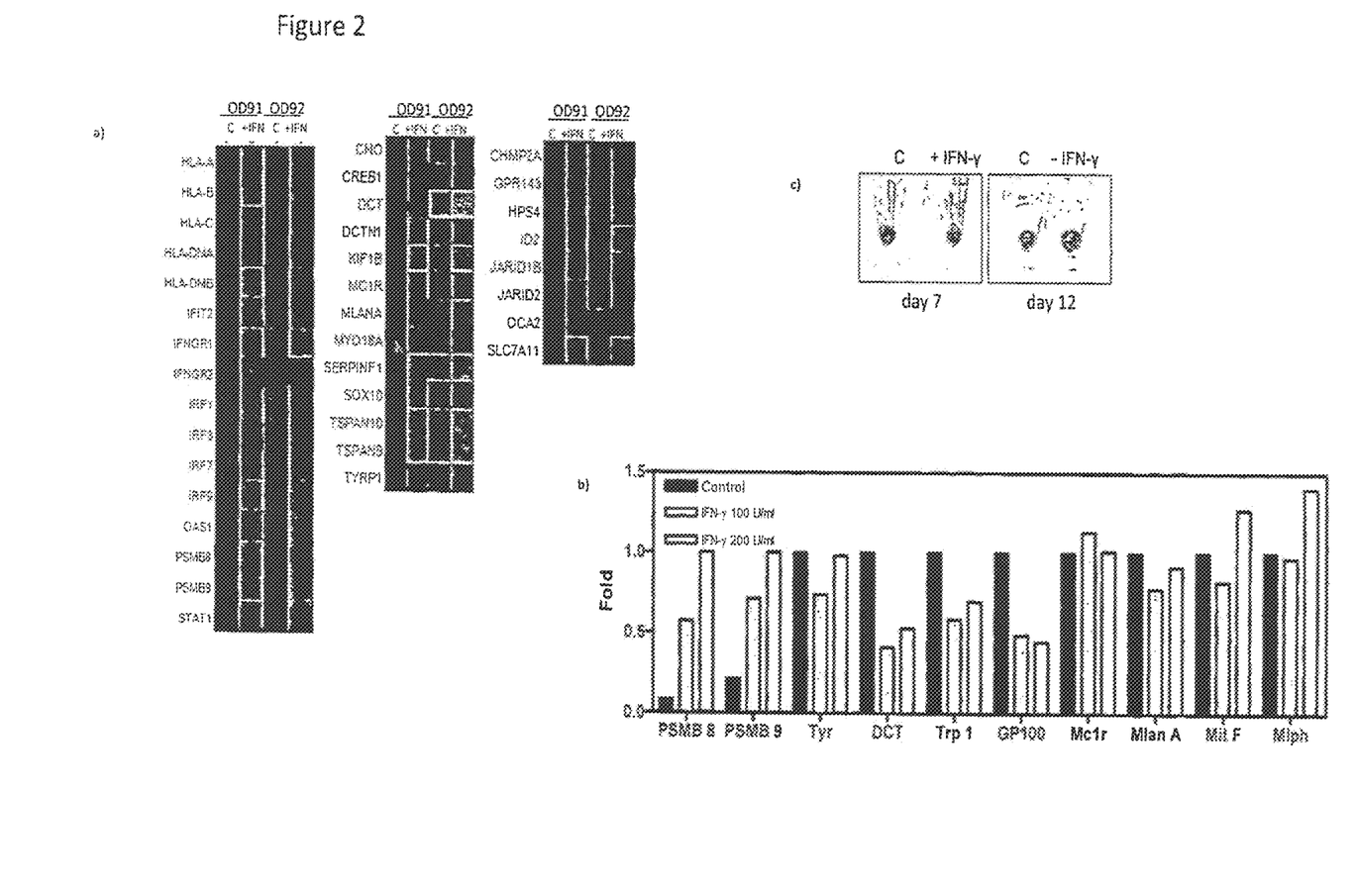

In order to understand the molecular changes induced by IFN-γ on melanocytes a microarray based study was carried out on two independent primary melanocyte cultures. Cells were treated with 100 U/ml of IFN-γ for 8 days (as mentioned in example 1) and total RNA was isolated and subjected to microarray. Microarray was performed using Illumina whole genome chip Human WG-6. RNA labelling was performed using Illumina total prep RNA labelling kit (Ambion). Subsequent hybridization and washing steps were carried out as per manufacturer's instructions. The data was average normalized; background subtracted and analyzed using Bead-studio software (Illumina). Typical of an immune cytokine IFN-γ elicited a gene expression profile suggestive of an immune response in melanocytes. However the pattern of gene expression also included suppression of certain pigmentation genes (FIG. 2). This confirmed that the hypopigmentory role of IFN-γ is due to the suppression of pigmentation genes by affecting the maturation of melanosomes. Regulation of chosen genes was confirmed by real-time PCR. In primary human melanocytes the regulation of multiple IFN-γ downstream genes were observed and is tabulated in table 1.

TABLE 1

List of genes regulated by IFN-γ in primary human melanocytes significantly regulated in primary melanocytes based on microarray DCT, TSPAN10, TSPAN9, SERPINF1, KIF1B, SOX10, MYO18A, MLANA, CREB1, MC1R, DCTNI, CNO, TYRP1, HPS4, GPR143, ID2, JARID2, OCA2 CHMP2A, JARID1B, SLC7A11, MCOLN3, IFT2, IFTM1, IRF1, IRF3, IRF4, IRF7, IRF9, OAS1, PSMB8, PSMB9, STAT1, STAT6, TNFRSF19, TNFSF12, IFNGR1, IFNGR2, MAPKAP1, LOC402221, PDK4, C19ORF28, FARSA, TSPAN4, TYSND1, DEAF1, PKN1, WHSC1L1, ACP1, RASSF1, FAM76B, XL, PGAM4, WDR26, PIK3CD, FEN1, HS.31532, NR1H2, DNAJB12, FEZ1, PWWP2B, TNFAIP1, SH3BGRL3, TCIRG1, PCMTD2, LOC643357, MYO1B, HS.374257, LOC648249, BIN1, HS.12876, PRMT1, JAK 1, JAK 2, HS.231861, BRD8, LOC347544, BANF1, GYPC, AGXT2L2, MORF4L1, MRRF, ACTB, OAS3, H1FX, UBE2G1, FAM10A4, C22ORF29, HLA, DRB4, TMEM69, C8ORF33, RCE1, HLAH, ARL6IP6, LOC402251, CYBA, HLAB, AHSA1, ERP29, ADAT3, PPT2, SCAND1, TNC, RPL32, IFIT3, GRN, CTTN, LOC648210, ARPC4, TBCC, CTH, HLAF, RIPK5, TAP2, GMPR, APRT, ACLY, TMED10, TUBA1A, AGPAT1, LOC407835, KIAA0460, PDIA6, PHF20L1, MRPL12, VAMP5, UBB, ARMCX1, BEX4, LOC441775, FAM152B, NAT5, OBFC2B, RAB4A, LOC440589, PHF5A, LRP11, TNPO1, STEAP1, LOC649150, CXORF40B, PTTG1IP, LOC284821, HP1BP3, CAPNS1, RNH1, HCG4, HS.406790, EEF1A1, HLA.DPA1, POLRMT, LOC388654, CPEB2, IFI27, GAA, ARFGEF1, RAB7L1

Example 3

To verify the pathway and elucidate the components of the pathway that mediate the hypopigmenting effect of IFN-γ we resorted to a siRNA based testing of protein functions. Primary human melanocytes were cultured in serum free media as described above (in example 1) and were transfected with 100 nM of siRNA (a mixture of 4 targeting siRNA from Dharmacon) that would target the component mRNA of interest using lipid based transfection reagent (Cellfectin II from Invitrogen). After the transfection the cells were trypsinized and plated in wells and were either treated with IFN-γ or left untreated as control. After 48 h of treatment, cells were lysed and total RNA was prepared from the cells and levels of the targeting gene transcript as well as that of DCT was measured by real-time PCR. Targeting siRNA to JAK-1, STAT-1 and IFNGR-1 substantially decreased the mRNA level of the cognate genes and concomitantly abrogated the IFN-γ mediated suppression of DCT transcript. This series of experiment further validated that the components of the pathway are potentially excellent targets for achieving altered pigmentation.

Example 4

IFN-γ is known to function in a species-specific manner. To verify whether the hypopigmentation observed in melanocytes is specifically brought about by IFN-γ; melanocytes were treated with mouse IFN-γ (100U/ml) and human IFN-γ (100U/ml) for 8 days. Mouse IFN-γ did not hypopigment human melanocytes confirming that the effect was specific and not a generic effect of peptide addition. When the human IFN-γ treated hypopigmented melanocytes were grown in the absence of the IFN-γ in M254 only, the cells were found to regain their pigmentation levels after 5 days, indicating reversibility of IFN-γ mediated hypopigmentaion in melanocytes. This supports IFN-γ to be an important component in mediating physiological reversible pigmentation changes.

Example 5

To probe for the causative role of IFN-γ in skin hypopigmenting conditions, RNA was isolated from the lesional hypopigmented and non-lesional epidermis of subjects with lepramatous leprosy. cDNA was synthesised and real-time PCR analysis performed for comparing gene expression changes between in pigmentation (TYR, TYRP1, TYRP2, MITF) genes and genes known to be upregulated by IFN-γ (PSMB8, PSMB9, HLA-DRB1, HLA-A, HLA-B, HLA-C, IFNGR1, IRF1). The expression levels of pigmentation genes including DCT (except MITF) was found to be less in the lesional skin of leprosy subjects, consistent with the visible hypopigmentaion. Concordant increase in IFN-γ gene signatures was also observed. Electron microscopic analysis of the non-lesional versus lesional skin also indicated the decrease in the number of mature (Stage III and IV) melanosomes in the lesional skin as compared to non-lesional skin. These results are concordant with our in vitro observations that IFN-γ stalls melanosomes in early stage of maturation, thereby leading to visible hypopigmentation. This study demonstrates that in diseased states this pathway could be operative to cause visible changes in human skin pigmentation.

Example 6

To understand the effect of IFN-γ on transfer of melanosomes from melanocytes to keratinocytes, cocultures of melanocytes and normal human epidermal keratinocytes (from Lonza or established from foreskin derived epidermis) were established in a ratio of 1:2. The cultures were maintained in 1:2 M254 and KSFM (Invitrogen) respectively in the presence or absence of IFN-γ (100U/ml) for 8 days. At the end of 8 days, keratinocytes were separated from melanocytes by differential trypsinization method and processed for electron microscopic analysis. Multiple micrographs of keratinocytes with melanosomes were obtained and analyzed for the number of melanosomes per micrograph. The cytoplasmic area of keratinocytes was calculated with image analysis software. Number of melanosomes/area of keratinocytes was observed to be decreased in keratinocytes which were grown in the presence of IFN-γ, indicating that IFN-γ inhibits the process of melanosome transfer to keratinocytes in addition to its effect on melanosome maturation.

TABLE 2

Prior art in relation to current claims

| S. No | Title | Reference | Major outcome of their study | Relevant results | Novelty in our patent |
|---|---|---|---|---|---|
| 1 | Upregulation of the IFN-gamma-stimulated genes in the development of delayed pigmented spots on the dorsal skin of F1 mice of HR-1 × HR/De. | J Invest Dermatol. 2005 May; 124(5): 1053-61. | Increase in the expression of interferon (IFN)-gamma-stimulated genes was detected in delayed pigmented lesions. Authors claim that IFN-gamma may play a pivotal role in the development of delayed pigmented spots in the mouse model of solar lentiges. | The study correlates interferon gamma signatures with pigmentation, however the involvement is in the development of delayed pigmented spots. | These studies are performed with mice which do not have epidermal pigmentation and apparently contradicts our study. |
| 2 | Interferon-gamma reduces melanosomal antigen expression and recognition of melanoma cells by cytotoxic T cells. | Am J Pathol. 2002 February; 160(2): 521-8. | IFN-gamma may enhance inflammatory responses yet hamper effective recognition of melanoma cells by the immune system | MART1, and GP100 antigen expression is decreased by IFN-γ in melanoma cells | This study does not reveal any new findings related to the pigmentation in the melanoma cells studied. Whereas our study divulges information about pigmentation regulation by interferon gamma in |

TABLE 2-continued

Prior art in relation to current claims

| S. No | Title | Reference | Major outcome of their study | Relevant results | Novelty in our patent |
|---|---|---|---|---|---|
| | | | | | melanocytes through melanosome maturation regulation |
| 3 | Interferon-gamma is a potent inducer of catagen-like changes in cultured human anagen hair follicles | Br J Dermatol. 2005 April; 152(4): 623-31. | Interferon gamma causes catagen like changes in human scalp follicular cells | Follicular melanogenesis is switched off in cells treated with interferon gamma | This study focusses on follicular cells which are distinct from melanocytes. Moreover the effect of interferon gamma herein requires cell cycle changes and pigmentation is a consequence. no evidence for melanosome maturation alterations are observed. |
| 4 | Antitumor activities of interferon alpha, beta, and gamma and their combinations on human melanoma cells in vitro: changes of proliferation, melanin synthesis, and immunophenotype. | J Invest Dermatol. 1990 December; 95 (6Suppl): 231S-237S. | Interferon beta causes potent antiproliferative effect on human melanoma cells. Cell surface antigens (HLA-DR and DQ) are altered upon interferon gamma treatment | Interferon alpha increases melanin synthesis and Interferon beta decreases melanin synthesis significantly. Melanin synthesis decreased observed with Interferon gamma but the data was not statistically significant | There was no information on the melanosome maturation and the process of pigmentation, which is a concerted effect of several distinct pathways. Our study demonstrates the effect of interferon gamma on many of these independent biochemical pathways. |

ADVANTAGES OF THE INVENTION

1) Application potential of this invention is immense in its ability to accomplish controlled hypopigmentation of the skin as it targets the entire process of melanosome maturation.

2) Small molecules inhibitors or antibody based neutralization of this pathway would be useful in treating pigmentation disorders like melasma, post-inflammatory hyperpigmentation, sun burn, UV induced hyperpigmentation, nevus, acanthosis nigricans etc.

3) Non-clinical, cosmetic application of the pathway could also be of use in modulating the skin tone in individuals 4) As interferon functions without affecting the levels of MITF pigmentation this strategy would be useful in conditions that increase pigmentation through MITF 5) IFN-γ or its derivative thereof can be formulated as a composition, for example, in a cream, gel or lotion for topical use or can be present as a liquid. The composition can also be present in dosage unit form that could be administered through sub-cutaneous infusion if necessary.

REFERENCES

1. Bennett, D. C., and Lamoreux, M. L. (2003). The color loci of mice—a genetic century. Pigment Cell Res 16, 333-344.
2. Carroll, J. M., Crompton, T., Seery, J. P., and Watt, F. M. (1997). Transgenic mice expressing IFN-gamma in the epidermis have eczema, hair hypopigmentation, and hair loss. J Invest Dermatol 108, 412-422.
3. Choi, W., Miyamura, Y., Wolber, R., Smuda, C., Reinhold, W., Liu, H., Kolbe, L., and Hearing, V. J. (2010). Regulation of human skin pigmentation in situ by repetitive UV exposure: molecular characterization of responses to UVA and/or UVB. J Invest Dermatol 130, 1685-1696.
4. Cui, R., Widlund, H. R., Feige, E., Lin, J. Y., Wilensky, D. L., Igras, V. E., D'Orazio, J., Fung, C. Y., Schanbacher, C. F., Granter, S. R., and Fisher, D. E. (2007). Central role of p53 in the suntan response and pathologic hyperpigmentation. Cell 128, 853-864.
5. Garbe, C., Krasagakis, K., Zouboulis, C. C., Schroder, K., Kruger, S., Stadler, R., and Orfanos, C. E. (1990). Antitumor activities of interferon alpha, beta, and gamma and their combinations on human melanoma cells in vitro: changes of proliferation, melanin synthesis, and immunophenotype. J Invest Dermatol 95, 231S-237S.
6. Gordon, P. R., Mansur, C. P., and Gilchrest, B. A. (1989). Regulation of human melanocyte growth, dendricity, and melanization by keratinocyte derived factors. J Invest Dermatol 92, 565-572.
7. Hu, Z. Z., Valencia, J. C., Huang, H., Chi, A., Shabanowitz, J., Hearing, V. J., Appella, E., and Wu, C. (2007). Comparative Bioinformatics Analyses and Profiling of Lysosome-Related Organelle Proteomes. Int J Mass Spectrom 259, 147-160.
8. Ito, T., Ito, N., Saathoff, M., Bettermann, A., Takigawa, M., and Paus, R. (2005). Interferon-gamma is a potent inducer of catagen-like changes in cultured human anagen hair follicles. Br J Dermatol 152, 623-631.
9. Jin, S. H., and Kang, H. Y. Activation of Toll-like Receptors 1, 2, 4, 5, and 7 on Human Melanocytes Modulate Pigmentation. Ann Dermatol 22, 486-489.
10. Jin, S. H., and Kang, H. Y. (2010). Activation of Toll-like Receptors 1, 2, 4, 5, and 7 on Human Melanocytes Modulate Pigmentation. Ann Dermatol 22, 486-489.
11. Le Poole, I. C., Riker, A. I., Quevedo, M. E., Stennett, L. S., Wang, E., Marincola, F. M., Kast, W. M., Robinson, J. K., and Nickoloff, B. J. (2002). Interferon-gamma reduces melanosomal antigen expression and recognition of melanoma cells by cytotoxic T cells. Am J Pathol 160, 521-528.
12. Martinez-Esparza, M., Ferrer, C., Castells, M. T., Garcia-Borron, J. C., and Zuasti, A. (2001). Transforming growth factor beta1 mediates hypopigmentation of B16 mouse melanoma cells by inhibition of melanin formation and melanosome maturation. Int J Biochem Cell Biol 33, 971-983.
13. Nihal, M., Ahmad, N., Mukhtar, H., and Wood, G. S. (2005). Anti-proliferative and proapoptotic effects of (−)-epigallocatechin-3-gallate on human melanoma: possible implications for the chemoprevention of melanoma. Int J Cancer 114, 513-521.
14. Nishimura, E. K., Suzuki, M., Igras, V., Du, J., Lonning, S., Miyachi, Y., Roes, J., Beermann, F., and Fisher, D. E. Key roles for transforming growth factor beta in melanocyte stem cell maintenance. Cell Stem Cell 6, 130-140.
15. Nishimura, E. K., Suzuki, M., Igras, V., Du, J., Lonning, S., Miyachi, Y., Roes, J., Beermann, F., and Fisher, D. E. (2010). Key roles for transforming growth factor beta in melanocyte stem cell maintenance. Cell Stem Cell 6, 130-140.
16. Richardson, J., Lundegaard, P. R., Reynolds, N. L., Dorin, J. R., Porteous, D. J., Jackson, I. J., and Patton, E. E. (2008). mc1r Pathway regulation of zebrafish melanosome dispersion. Zebrafish 5, 289-295.
17. Sarra, M., Caruso, R., Cupi, M. L., Monteleone, I., Stolfi, C., Campione, E., Diluvio, L., Mazzotta, A., Botti, E., Chimenti, S., et al. (2011). IL-21 promotes skin recruitment of CD4(+) cells and drives IFN-gamma-dependent epidermal hyperplasia. J Immunol 186, 5435-5442.
18. Scott, G. A., Jacobs, S. E., and Pentland, A. P. (2006). sPLA2-X stimulates cutaneous melanocyte dendricity and pigmentation through a lysophosphatidylcholine-dependent mechanism. J Invest Dermatol 126, 855-861.
19. Seiberg, M., Paine, C., Sharlow, E., Andrade-Gordon, P., Costanzo, M., Eisinger, M., and Shapiro, S. S. (2000) Inhibition of melanosome transfer results in skin lightening. J Invest Dermatol 115, 162-167.
20. Sturm, R. A. (2009). Molecular genetics of human pigmentation diversity. Hum Mol Genet 18, R9-17.
21. Yamaguchi, Y., Brenner, M., and Hearing, V. J. (2007). The regulation of skin pigmentation. J Biol Chem 282, 27557-27561.
22. Yamaguchi, Y., and Hearing, V. J. (2009). Physiological factors that regulate skin pigmentation. Biofactors 35, 193-199.
23. Yamaguchi, Y., Morita, A., Maeda, A., and Hearing, V. J. (2009). Regulation of skin pigmentation and thickness by Dickkopf 1 (DKK1). J Investig Dermatol Symp Proc 14, 73-75.

We claim:

1. A method to alter stage I and II melanosome maturation in normal epidermal melanocytes of a subject by contacting the normal epidermal melanocytes with IFN-γ,
   wherein the normal epidermal melanocytes are treated with 300 to 500 U/ml of IFN-γ for 8 days,
   wherein the IFN-γ increases expression of IFN-γ pathway components selected from the group consisting of interferon gamma receptor 1 (IFNGR1), janus kinase 1 (JAK1), and signal transducer and activator of transcription 1 (STAT1).

2. The method as claimed in claim 1 wherein IFN-γ alters the levels of tyrosinase (TYR), dopachrome tautomerase (TYRP2/DCT), cappuccino protein (CNO), Hermansky-Pudlak syndrome 4 protein homolog (HPS4), G-protein coupled receptor 143 (GPR143), oculocutaneous albinism 2 gene (OCA2), solute carrier family 7 member 11 gene (SLC7A11), and mucolipin 3 gene (MCOLN3).

3. The method as claimed in claim 1 wherein the transfer of melanosome to keratinocytes is altered by targeting components of the IFN-γ pathway selected from the group comprising of interferon gamma (IFNG), interferon gamma receptor 1 (IFNGR1), janus kinase 1 (JAK1), and signal transducer and activator of transcription 1 (STAT1).

4. The method as claimed in claim 1, wherein the normal epidermal melanocytes are treated with 300 U/ml of IFN-γ.

5. The method as claimed in claim 1, wherein the normal epidermal melanocytes are treated with 400 U/ml of IFN-γ.

6. The method as claimed in claim 1, wherein the normal epidermal melanocytes are treated with 500 U/ml of IFN-γ.

7. A method of treating skin pigmentation in normal epidermal melanocytes of a subject by contacting the normal epidermal melanocytes with IFN-γ,
   wherein the normal epidermal melanocytes are treated with 300 to 500 U/ml of IFN-γ for 8 days,
   wherein the IFN-γ increases expression of IFN-γ pathway components selected from the group consisting of interferon gamma receptor 1 (IFNGR1), janus kinase 1 (JAK1), and signal transducer and activator of transcription 1 (STAT1).

8. The method as claimed in claim 7 wherein IFN-γ is administered to the subject by topical delivery or by sub-cutaneous delivery.

9. The method as claimed in claim 8 wherein the topical delivery or sub-cutaneous delivery is in a dosage form selected from the group comprising, a powder, a solution, an emulsion, a fluid emulsion, a suspension, a fluid suspension, a semi-solid, an ointment, a paste, a cream, a gel, a jelly, a foam, an implant, an injection, a patch and a spray.

10. The method as claimed in claim 7 useful for treating skin disorders selected from the group comprising of hyperpigmentation, hypopigmentation, uneven pigmentation, post inflammatory pigmentation, sun-damaged skin, pigmented birthmark, acanthosis nigricans and solar lentiges, age-related pigmentation changes, indeterminate leprosy, tuberculoid leprosy, borderline leprosy, leprematous leprosy.

* * * * *

SEQUENCE LISTING

```
<160> NUMBER OF SEQ ID NOS: 39

<210> SEQ ID NO 1
<211> LENGTH: 20
<212> TYPE: DNA
<213> ORGANISM: Artificial
<220> FEATURE:
<223> OTHER INFORMATION: Homo sapiens melanocortin 1 receptor (alpha
      melanocyte stimulating hormone receptor) (MC1R) Forward primer

<400> SEQUENCE: 1
tgcaaaagga ggtgaaatcc                                                 20

<210> SEQ ID NO 2
<211> LENGTH: 20
<212> TYPE: DNA
<213> ORGANISM: Artificial
<220> FEATURE:
<223> OTHER INFORMATION: Homo sapiens melanocortin 1 receptor (alpha
      melanocyte stimulating hormone receptor) (MC1R) Reverse primer

<400> SEQUENCE: 2
agtgcccagt ctgagcctta                                                 20

<210> SEQ ID NO 3
<211> LENGTH: 20
<212> TYPE: DNA
<213> ORGANISM: Artificial
<220> FEATURE:
<223> OTHER INFORMATION: Homo sapiens melan-A (MLANA), Forward primer

<400> SEQUENCE: 3
gatcatcggg acagcaaagt                                                 20

<210> SEQ ID NO 4
<211> LENGTH: 20
<212> TYPE: DNA
<213> ORGANISM: Artificial
<220> FEATURE:
<223> OTHER INFORMATION: Homo sapiens melan-A (MLANA), Reverse primer
```

```
<400> SEQUENCE: 4
aggtgtctcg ctggctctta                                               20

<210> SEQ ID NO 5
<211> LENGTH: 20
<212> TYPE: DNA
<213> ORGANISM: Artificial
<220> FEATURE:
<223> OTHER INFORMATION: Homo sapiens microphthalmia-associated
      transcription factor (MITF), transcript variant 5. Forward primer

<400> SEQUENCE: 5
ccaggcatga acacacattc                                               20

<210> SEQ ID NO 6
<211> LENGTH: 20
<212> TYPE: DNA
<213> ORGANISM: Artificial
<220> FEATURE:
<223> OTHER INFORMATION: Homo sapiens microphthalmia-associated
      transcription factor (MITF), transcript variant 5 Reverse primer

<400> SEQUENCE: 6
tccatcaagc ccaagatttc                                               20

<210> SEQ ID NO 7
<211> LENGTH: 20
<212> TYPE: DNA
<213> ORGANISM: Artificial
<220> FEATURE:
<223> OTHER INFORMATION: Homo sapiens melanophilin (MLPH), Forward
      primer

<400> SEQUENCE: 7
gacagcgacc agacagatga                                               20

<210> SEQ ID NO 8
<211> LENGTH: 20
<212> TYPE: DNA
<213> ORGANISM: Artificial
<220> FEATURE:
<223> OTHER INFORMATION: Homo sapiens melanophilin (MLPH), Reverse
      primer

<400> SEQUENCE: 8
gaccttgagg ctgagtggag                                               20

<210> SEQ ID NO 9
<211> LENGTH: 20
<212> TYPE: DNA
<213> ORGANISM: Artificial
<220> FEATURE:
<223> OTHER INFORMATION: Homo sapiens dopachrometautomerase (dopachrome
      delta-isomerase, tyrosine-related protein 2) (DCT), Forward primer

<400> SEQUENCE: 9
gaacactggt ggctttggtt                                               20

<210> SEQ ID NO 10
<211> LENGTH: 20
<212> TYPE: DNA
<213> ORGANISM: Artificial
<220> FEATURE:
<223> OTHER INFORMATION: Homo sapiens dopachrometautomerase (dopachrome
      delta-isomerase, tyrosine-related protein 2) (DCT), Reverse Primer

<400> SEQUENCE: 10
```
ggtaaggcat gagcaccta                                              20

<210> SEQ ID NO 11
<211> LENGTH: 20
<212> TYPE: DNA
<213> ORGANISM: Artificial
<220> FEATURE:
<223> OTHER INFORMATION: Homo sapiens tyrosinase-related protein 1
      (TYRP1), Forward primer

<400> SEQUENCE: 11
agcagtagtt ggcgctttgt                                             20

<210> SEQ ID NO 12
<211> LENGTH: 20
<212> TYPE: DNA
<213> ORGANISM: Artificial
<220> FEATURE:
<223> OTHER INFORMATION: Homo sapiens tyrosinase-related protein 1
      (TYRP1), Reverse Primer

<400> SEQUENCE: 12
tcagtgagga gaggctggtt                                             20

<210> SEQ ID NO 13
<211> LENGTH: 20
<212> TYPE: DNA
<213> ORGANISM: Artificial
<220> FEATURE:
<223> OTHER INFORMATION: Homo sapiens tyrosinase (oculocutaneous
      albinism IA Forward primer

<400> SEQUENCE: 13
ttgtactgcc tgctgtggag                                             20

<210> SEQ ID NO 14
<211> LENGTH: 20
<212> TYPE: DNA
<213> ORGANISM: Artificial
<220> FEATURE:
<223> OTHER INFORMATION: Homo sapiens tyrosinase (oculocutaneous
      albinism IA Reverse Primer

<400> SEQUENCE: 14
caggaacctc tgcctgaaag                                             20

<210> SEQ ID NO 15
<211> LENGTH: 20
<212> TYPE: DNA
<213> ORGANISM: Artificial
<220> FEATURE:
<223> OTHER INFORMATION: HUMAN STAT1 Forward primer

<400> SEQUENCE: 15
ttcaggaaga cccaatccag                                             20

<210> SEQ ID NO 16
<211> LENGTH: 20
<212> TYPE: DNA
<213> ORGANISM: Artificial
<220> FEATURE:
<223> OTHER INFORMATION: HUMAN STAT1. Reverse Primer

<400> SEQUENCE: 16
tgaatattcc ccgactgagc                                             20

```
<210> SEQ ID NO 17
<211> LENGTH: 20
<212> TYPE: DNA
<213> ORGANISM: Artificial
<220> FEATURE:
<223> OTHER INFORMATION: HUMAN JAK1 Forward primer

<400> SEQUENCE: 17
tgctcctgag tgtgttgagg                                          20

<210> SEQ ID NO 18
<211> LENGTH: 20
<212> TYPE: DNA
<213> ORGANISM: Artificial
<220> FEATURE:
<223> OTHER INFORMATION: HUMAN JAK1 Reverse Primer

<400> SEQUENCE: 18
aggtcagcca gctccttaca                                          20

<210> SEQ ID NO 19
<211> LENGTH: 20
<212> TYPE: DNA
<213> ORGANISM: Artificial
<220> FEATURE:
<223> OTHER INFORMATION: HUMAN JAK2 Forward primer

<400> SEQUENCE: 19
gagcctatcg gcatggaata                                          20

<210> SEQ ID NO 20
<211> LENGTH: 20
<212> TYPE: DNA
<213> ORGANISM: Artificial
<220> FEATURE:
<223> OTHER INFORMATION: HUMAN JAK2 Reverse Primer

<400> SEQUENCE: 20
actgccatcc caagacattc                                          20

<210> SEQ ID NO 21
<211> LENGTH: 22
<212> TYPE: DNA
<213> ORGANISM: Artificial
<220> FEATURE:
<223> OTHER INFORMATION: Human IFNGR1 Forward primer

<400> SEQUENCE: 21
catcacgtca taccagccat tt                                       22

<210> SEQ ID NO 22
<211> LENGTH: 22
<212> TYPE: DNA
<213> ORGANISM: Artificial
<220> FEATURE:
<223> OTHER INFORMATION: Human IFNGR1 Reverse Primer

<400> SEQUENCE: 22
ctggattgtc ttcggtatgc at                                       22

<210> SEQ ID NO 23
<211> LENGTH: 20
<212> TYPE: DNA
<213> ORGANISM: Artificial
<220> FEATURE:
<223> OTHER INFORMATION: Human IFNGR2 Forward primer
```

-continued

<400> SEQUENCE: 23
atcagcgatg tcaaagggag                                              20

<210> SEQ ID NO 24
<211> LENGTH: 20
<212> TYPE: DNA
<213> ORGANISM: Artificial
<220> FEATURE:
<223> OTHER INFORMATION: Human IFNGR2 Reverse Primer

<400> SEQUENCE: 24
tgacaatgcc ttggtttcaa                                              20

<210> SEQ ID NO 25
<211> LENGTH: 20
<212> TYPE: DNA
<213> ORGANISM: Artificial
<220> FEATURE:
<223> OTHER INFORMATION: Human IRF1 Forward primer

<400> SEQUENCE: 25
aagtccagcc gagatgctaa                                              20

<210> SEQ ID NO 26
<211> LENGTH: 20
<212> TYPE: DNA
<213> ORGANISM: Artificial
<220> FEATURE:
<223> OTHER INFORMATION: Human IRF1 Reverse Primer

<400> SEQUENCE: 26
tagctgctgt ggtcatcagg                                              20

<210> SEQ ID NO 27
<211> LENGTH: 20
<212> TYPE: DNA
<213> ORGANISM: Artificial
<220> FEATURE:
<223> OTHER INFORMATION: Human IRF3 Forward primer

<400> SEQUENCE: 27
tcagggcctt ggtagaaatg                                              20

<210> SEQ ID NO 28
<211> LENGTH: 20
<212> TYPE: DNA
<213> ORGANISM: Artificial
<220> FEATURE:
<223> OTHER INFORMATION: Human IRF3 Reverse Primer

<400> SEQUENCE: 28
gcaggtaggc cttgtactgg                                              20

<210> SEQ ID NO 29
<211> LENGTH: 20
<212> TYPE: DNA
<213> ORGANISM: Artificial
<220> FEATURE:
<223> OTHER INFORMATION: Human IRF4 Forward primer

<400> SEQUENCE: 29
ttaccaccaa gggcaggtag                                              20

<210> SEQ ID NO 30

```
<211> LENGTH: 20
<212> TYPE: DNA
<213> ORGANISM: Artificial
<220> FEATURE:
<223> OTHER INFORMATION: Human IRF4 Reverse Primer

<400> SEQUENCE: 30
aaagccaaga ggtgcgagta                                                  20

<210> SEQ ID NO 31
<211> LENGTH: 20
<212> TYPE: DNA
<213> ORGANISM: Artificial
<220> FEATURE:
<223> OTHER INFORMATION: Human IRF7 Forward primer

<400> SEQUENCE: 31
taccatctac ctgggcttcg                                                  20

<210> SEQ ID NO 32
<211> LENGTH: 20
<212> TYPE: DNA
<213> ORGANISM: Artificial
<220> FEATURE:
<223> OTHER INFORMATION: Human IRF7 Reverse Primer

<400> SEQUENCE: 32
tgctgctatc cagggaagac                                                  20

<210> SEQ ID NO 33
<211> LENGTH: 20
<212> TYPE: DNA
<213> ORGANISM: Artificial
<220> FEATURE:
<223> OTHER INFORMATION: Human IRF9
      Forward primer

<400> SEQUENCE: 33
gctgctccca atgtctgaat                                                  20

<210> SEQ ID NO 34
<211> LENGTH: 20
<212> TYPE: DNA
<213> ORGANISM: Artificial
<220> FEATURE:
<223> OTHER INFORMATION: Human IRF9
      Forward primer

<400> SEQUENCE: 34
gctgctccca atgtctgaat                                                  20

<210> SEQ ID NO 35
<211> LENGTH: 20
<212> TYPE: DNA
<213> ORGANISM: Artificial
<220> FEATURE:
<223> OTHER INFORMATION: Human IRF9 Reverse Primer

<400> SEQUENCE: 35
aggaaggagg aagaggatgc                                                  20

<210> SEQ ID NO 36
<211> LENGTH: 22
<212> TYPE: DNA
<213> ORGANISM: Artificial
<220> FEATURE:
<223> OTHER INFORMATION: Human PSMB8 Forward primer
```

```
<400> SEQUENCE: 36
tcgccttcaa gttccagcat gg                                                22

<210> SEQ ID NO 37
<211> LENGTH: 22
<212> TYPE: DNA
<213> ORGANISM: Artificial
<220> FEATURE:
<223> OTHER INFORMATION: Human PSMB8 Reverse Primer

<400> SEQUENCE: 37
ccaaccatct tccttcatgt gg                                                22

<210> SEQ ID NO 38
<211> LENGTH: 22
<212> TYPE: DNA
<213> ORGANISM: Artificial
<220> FEATURE:
<223> OTHER INFORMATION: Human PSMB9 Forward primer

<400> SEQUENCE: 38
ttgtgatggg ttctgattcc cg                                                22

<210> SEQ ID NO 39
<211> LENGTH: 20
<212> TYPE: DNA
<213> ORGANISM: Artificial
<220> FEATURE:
<223> OTHER INFORMATION: Human PSMB9 Reverse Primer

<400> SEQUENCE: 39
cagagcaata gcgtctgtgg                                                   20
```